(12) United States Patent
Limburg et al.

(10) Patent No.: US 6,966,665 B2
(45) Date of Patent: Nov. 22, 2005

(54) FLAMELESS CANDLE WITH AIR INTAKE CHAMBER AND AIR OUTFLOW CHAMBER

(75) Inventors: James A. Limburg, Racine, WI (US); Thomas J. Szymczak, Franksville, WI (US); Milan L. Zdrubecky, Milwaukee, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 10/608,199

(22) Filed: Jun. 27, 2003

(65) Prior Publication Data

US 2004/0264169 A1 Dec. 30, 2004

(51) Int. Cl.⁷ ............................................. F21V 33/00
(52) U.S. Cl. .................... 362/96; 362/161; 362/392; 362/806
(58) Field of Search ................... 362/96, 161, 806, 362/810, 392; 416/5

(56) References Cited

U.S. PATENT DOCUMENTS

| | | | |
|---|---|---|---|
| 2,435,811 A | 2/1948 | Waters ........................ 240/10 |
| 2,557,501 A | 6/1951 | Fusay, et al. | |
| 2,828,953 A | 4/1958 | Hartmann ..................... 261/30 |
| 3,080,624 A | 3/1963 | Weber, III | |
| 3,748,464 A | 7/1973 | Andeweg ................ 240/108 R |
| 3,749,904 A | 7/1973 | Graff ........................ 240/10 B |
| 3,761,702 A | 9/1973 | Andeweg ..................... 240/2 R |
| 3,790,081 A | 2/1974 | Thornton et al. .............. 239/55 |
| 3,890,085 A | 6/1975 | Andeweg | |
| 3,923,458 A | 12/1975 | Moran | |
| 3,948,445 A | 4/1976 | Andeweg | |
| 3,990,848 A | 11/1976 | Corris ........................ 21/126 |
| 3,993,444 A | 11/1976 | Brown ........................ 21/126 |
| 4,035,451 A | 7/1977 | Tringali ....................... 261/101 |
| 4,166,087 A | 8/1979 | Cline et al. .................... 261/96 |
| 4,276,236 A | 6/1981 | Sullivan et al. ................ 261/30 |
| 4,294,778 A | 10/1981 | DeLuca ........................ 261/30 |
| 4,323,193 A | 4/1982 | Compton et al. .............. 239/44 |
| 4,346,059 A | 8/1982 | Spector | |
| 4,383,951 A | 5/1983 | Palson .......................... 261/30 |
| 4,432,938 A | 2/1984 | Meetze, Jr. ................... 422/49 |
| 4,493,011 A | 1/1985 | Spector | |

(Continued)

FOREIGN PATENT DOCUMENTS

| | | | |
|---|---|---|---|
| AU | 664685 | 11/1995 | ............ A61L/9/12 |
| EP | 0 882 459 | 12/1998 | ............ A61L/9/03 |
| EP | 1 283 062 | 2/2003 | ............ A61L/9/03 |
| GB | 2 285 579 | 7/1995 | ............ A61L/9/12 |
| WO | WO 95/10352 | 4/1995 | ............ B01F/3/04 |
| WO | DM/054926 | 9/2000 | |
| WO | WO 01/02025 | 1/2001 | ............ A61L/9/12 |
| WO | WO 01/23008 | 4/2001 | ............ A61L/9/12 |
| WO | WO 02/30220 | 4/2002 | ........... A24F/25/00 |
| WO | WO 02/31413 | 4/2002 | ............ A24F/6/00 |
| WO | WO 03/086487 | 10/2003 | ............ A61L/9/03 |

OTHER PUBLICATIONS

"INGLOW™ Candle Company" www.inglowcandle.com (2002).

(Continued)

*Primary Examiner*—Sandra O'Shea
*Assistant Examiner*—Mark Tsidulko

(57) ABSTRACT

A flameless candle includes a housing, which defines an enclosure. A wall is positioned in the enclosure to form an air intake chamber and an air outflow chamber. At least one opening is in communication with both the ambient air and the air intake chamber. At least one opening is in communication with the air intake chamber and the air outflow chamber. And at least one opening is in communication with the ambient air and the air outflow chamber.

49 Claims, 5 Drawing Sheets

U.S. PATENT DOCUMENTS

| | | | |
|---|---|---|---|
| 4,621,768 A | 11/1986 | Lhoste et al. | 239/44 |
| 4,660,764 A | 4/1987 | Joyaux et al. | 239/44 |
| 4,666,638 A | 5/1987 | Baker et al. | 261/26 |
| 4,695,435 A | 9/1987 | Spector | 422/124 |
| 4,707,338 A | 11/1987 | Spector | 422/124 |
| 4,739,928 A | 4/1988 | O'Neil | 239/45 |
| 4,743,406 A | 5/1988 | Steiner et al. | 261/30 |
| 4,857,240 A | 8/1989 | Kearnes et al. | 261/26 |
| 4,866,580 A | 9/1989 | Blackerby | |
| 4,913,350 A | 4/1990 | Purzycki | |
| 4,931,224 A | 6/1990 | Holzner, Sr. | 261/30 |
| 4,968,487 A | 11/1990 | Yamamoto et al. | 422/125 |
| RE33,864 E | 3/1992 | Steiner | 261/30 |
| 5,114,625 A | 5/1992 | Gibson | 261/30 |
| 5,126,078 A | 6/1992 | Steiner et al. | 261/26 |
| 5,133,042 A | 7/1992 | Pelonis | 392/365 |
| 5,217,696 A | 6/1993 | Wolverton et al. | |
| 5,223,182 A | 6/1993 | Steiner et al. | 261/26 |
| 5,342,584 A | 8/1994 | Fritz et al. | 422/124 |
| 5,370,829 A | 12/1994 | Kunze | 261/24 |
| 5,376,338 A | 12/1994 | Zlotnik | 422/124 |
| 5,547,616 A | 8/1996 | Dancs et al. | 261/26 |
| 5,647,053 A | 7/1997 | Schroeder et al. | 392/390 |
| 5,651,942 A | 7/1997 | Christensen | 422/125 |
| 5,662,835 A | 9/1997 | Collingwood | 261/26 |
| D386,974 S | 12/1997 | Wefler | D9/569 |
| 5,891,400 A | 4/1999 | Ansari et al. | |
| 5,909,845 A | 6/1999 | Greatbatch et al. | 239/44 |
| 5,970,643 A | 10/1999 | Gawel, Jr. | 43/1 |
| 5,980,064 A | 11/1999 | Metroyanis | 362/194 |
| 6,017,139 A | 1/2000 | Lederer | |
| 6,104,867 A | 8/2000 | Stathakis et al. | 392/403 |
| 6,106,786 A | 8/2000 | Akahoshi | |
| 6,196,706 B1 | 3/2001 | Cutts | 362/392 |
| 6,354,710 B1 | 3/2002 | Nacouzi | 362/96 |
| 6,361,752 B1 | 3/2002 | Demarest et al. | 422/306 |
| 6,371,450 B1 | 4/2002 | Davis et al. | 261/26 |
| 6,454,425 B1 * | 9/2002 | Lin | 362/96 |
| 6,555,068 B2 | 4/2003 | Smith | 422/123 |
| 6,616,308 B2 | 9/2003 | Jensen et al. | 362/351 |
| 2002/0080601 A1 * | 6/2002 | Meltzer | 362/96 |
| 2002/0093834 A1 | 7/2002 | Yu et al. | 362/565 |
| 2002/0136886 A1 | 9/2002 | He et al. | 428/313.5 |
| 2003/0007887 A1 | 1/2003 | Roumpos, et al. | |
| 2003/0053305 A1 | 3/2003 | Lin | |
| 2003/0146292 A1 | 8/2003 | Schramm et al. | 239/4 |
| 2004/0141315 A1 | 7/2004 | Sherburne | 362/161 |
| 2004/0196658 A1 | 10/2004 | Fung | |
| 2004/0246711 A1 | 12/2004 | Brenchley et al. | 362/161 |
| 2004/0257998 A1 | 12/2004 | Hart et al. | |

OTHER PUBLICATIONS

Int'l Search Report dated Aug. 16, 2004, Application No. PCT/US04/008436.

Int'l Search Report dated Aug. 16, 2004, Application No. PCT/US04/008437.

"Luna Candles" http://www.epartyunlimited.com/luna-candles.html (print date 2004).

* cited by examiner

US 6,966,665 B2

FLAMELESS CANDLE WITH AIR INTAKE CHAMBER AND AIR OUTFLOW CHAMBER

FIELD OF THE INVENTION

The application relates to candles and, more particularly, to flameless candles.

DETAILED DESCRIPTION

Shortcomings of the existing art are overcome through the provision of a flameless candle with an air intake chamber and an air outflow chamber.

In one example a flameless candle is provided. The flameless candle comprises a housing defining an enclosure. A wall is positioned in the enclosure to form an air intake chamber and an air outflow chamber. At least one opening is in communication with both the air intake chamber and the air outflow chamber. At least one opening is in communication with the air intake chamber and the ambient air. Finally, at least one opening is in communication with the air outflow chamber and the ambient air.

In another example, a flameless candle is provided. The flameless candle encloses a fan that generates an air stream. A wick is positioned at least partially in the air stream. A wax covered sidewall defines an enclosure that contains the fan and the wick.

In yet another example, a flameless candle is provided with a wax covered housing defining an enclosure. A wall is positioned in the enclosure to form an air intake chamber and an air outflow chamber in the enclosure. An opening in the wax covered housing is in communication with the air intake chamber and the air outflow chamber. A lid is positioned in the enclosure.

These and other features will become apparent from the following detailed description, the accompanying drawings, and the claims.

Figure 1:
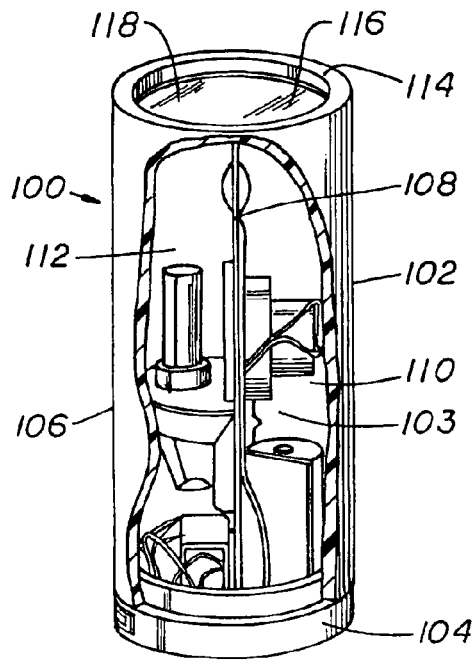
FIG. 1 is a side perspective view of one example of a flameless candle with a portion of the sidewall of the housing cut away.

Turning to FIG. 1, one example of a flameless candle 100 is now provided for illustrative purposes. Flameless candle 100, in one example, comprises a housing 102, which defines an enclosure 103. Housing 102 includes a base 104 and a sidewall 106. In one example base 104 is circular and sidewall 106 is cylindrical. Alternatively, base 104 and sidewall 106 could be another shape, such as square, rectangular, octagonal, etc. depending on the needs of the manufacturers, consumers, retailers, etc.

The respective planes of base 104 and sidewall 106 extend perpendicular to each other. It should be noted, however, that the respective planes of base 104 and sidewall 106 could have another relationship depending on the shape of flameless candle 100. For example, if flameless candle 100 were triangular, sidewall 106 would define two planes that intersected base 104 at an angle.

A wall 108 is positioned in enclosure 103 and thereby forms an air intake chamber 10 and an air outflow chamber 112. In one example, wall 108 is positioned between the two opposing sides of base 104. In another example, wall 108 is positioned equidistant from the two opposing sides of base 104. A plane of wall 108 extends perpendicular to the plane of base 104. In another example, the plane of wall 108 could meet the plane of base 104 at an angle. Such a relationship may be desirable if, for example, flameless candle 100 were shaped differently, or if a designer wanted to shape air intake chamber 110 and air outflow chamber 112 differently to achieve a particular air flow throughout flameless candle 100. In another example, wall 108 could be positioned parallel to base 104, thereby dividing enclosure 103 into an upper chamber and a lower chamber. Either the upper chamber or lower chamber could then serve as air intake chamber 110 and air outflow chamber 112, and vice versa.

Wall 108 in one example is attached to base 104 using an adhesive. In another example, wall 108 is attached to base 104 using mechanical means, such as screws, brackets, etc. In yet another example, wall 108 is removeably attached to base 104, for example, by providing base 108 with grooves and frictionally securing wall 108 in the grooves. In a further example wall 108 is made integral with base 104, such as by molding the two together.

Referring further to FIG. 1, air intake chamber 110 and air outflow chamber 112 are in communication with the ambient air through an opening at the top portion 114 of flameless candle 100. In one example, the periphery of sidewall 106 and wall 108 define two openings 116, 118, one in communication with air intake chamber 110 and one in communication with air outflow chamber 112, respectively. In another example, a wax covered lid having its own openings is placed over openings 116, 118, as will be discussed herein. Regardless of the particular configuration, ambient air is drawn into air intake chamber 110 and fragrant air is expelled from air outflow chamber 112, as will be further discussed herein.

Figure 2:
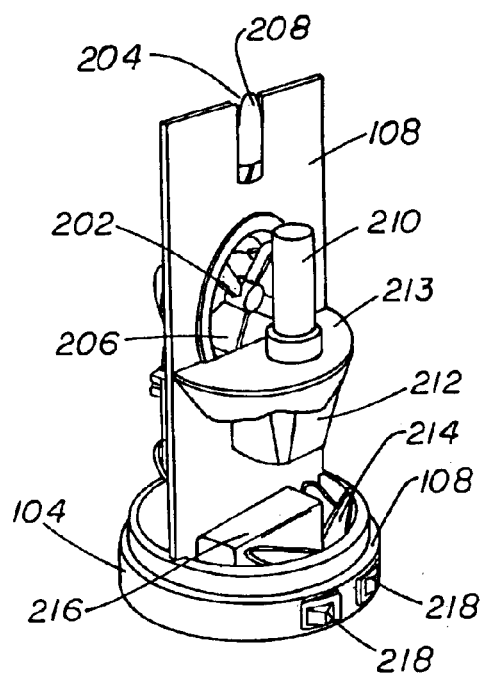
FIG. 2 is a front perspective view of the flameless candle of FIG. 1 with the sidewall of the housing removed.

FIG. 2 shows a front perspective view of flameless candle 100 with sidewall 106 removed. Referring to FIGS. 1 and 2, wall 108 contains two openings 202, 204. Openings 202 and 204 are in communication with air intake chamber 110 and air outflow chamber 112 shown in FIG. 1. Opening 202 in one example holds fan 206. Opening 202 allows air to circulate from air intake chamber 110 to air outflow chamber 112. Opening 204, in one example, holds light bulb 208. Opening 202 also serves to allow light to enter both air intake chamber 110 and air outflow chamber 112. Thus, light can be evenly distributed throughout enclosure 103.

Light bulb 208 serves as a light source to distribute light throughout enclosure 103 and to the eye of an observer. Accordingly, flameless candle 100 will appear as if a flame is flickering therein. Light bulb 208 could be a flickering light bulb or a constant light bulb 208. Furthermore, flameless candle 100 could contain electronics to cause light bulb 208 to flicker or remain constant. The electronics could also be program light bulb 208 could to perform combinations of flickering, remaining constant, etc. Light bulb 208 could provide plain white light or could be colored. A second light bulb 208 could be added to provide a combination of colored and white light. Electronics could be used to vary the emission of the colored and white light. It should be noted also that another light source, such as fiber optics, could be used in place of light bulb 108 or light bulb 208 could be omitted altogether. The particular choice of whether to provide flameless candle 100 with a light source, and if so, what type of light source, will depend on the goals and needs of the manufacturer, seller, and consumer.

Referring further to FIG. 2, a wick 210 and volatile fragrance source 212 are mounted to wall 108. In one example, wick 210 and fragrance source 212 are mounted to wall 108 through employment of mounting bracket 213. Alternatively, wick 210 and fragrance source 212 could be mounted to wall 108 through used of another connector, such as an adhesive, screws, etc. Wick 210 and fragrance source 212 are positioned in air outflow chamber 112 such that wick 210 is located in an air stream created by fan 206.

Wick 210 in one example is formed from a plastic material such as nylon, or in particular ultra high molecular weight, high density polyethylene (HDPE). Alternatively, wick 210 could be formed from another material (e.g., cotton, fiber, capillary, stone, ceramic, etc.) Fragrance source 212 in one example is a liquid dispenser that is designed to disseminate a volatile liquid, such as a fragrance compound, into a room. The fragrance compound emanates from wick 210 at room ambient temperature and is moved into the ambient air via the generated air stream.

Wick 210 and fragrance source 212 can release a fragrance in a variety of ways. For example, wick 210 and fragrance source could be episodic, meaning that a fragrance is only released for a short period of time, such as a few hours or even minutes. Alternatively, wick 210 and fragrance source 212 could release a fragrance for longer periods of time, such as days, weeks, or months. The longevity of wick 210 and/or fragrance source 212 will depend on the needs of the designers, manufacturers, buyers, and consumers. It should also be noted that wick 210 and fragrance source 212 could be replaced by another device that emanates a fragrance (e.g., gels, solids, fogs, aerosols, etc.), as long as the device that produces the fragrance is positioned such that the fragrance is placed in the air stream created by fan 206.

Further referring to FIG. 2, base 104 and one end of wall 108 form compartment 214. Compartment 214, in one example, is utilized to hold power source 216. Power source 216, in one example, is a nine volt battery. It should be noted, however, that other power sources (e.g., AA batteries, C batteries, D batteries, DC adaptors, plug-ins, rechargers, etc.) could be used. Power source 216 drives fan 206 and/or light bulb 208. In another example, compartment 214 could be used for storage of additional wicks, fragrance sources, etc. Switches 218 are provided to activate fan 206 and light bulb 208.

It should be noted that fan 206 does not necessarily have to be motor driven. Fan 206 could be hand or wind drive. In addition, fan could be replaced by any device that is capable of producing an air stream sufficient to propel fragrant air out of flameless candle 100. It should also be noted that fan 206 could designed to operate continuously or intermittently. The particular choice of fan 206 will depend on the objectives of the designers, manufacturers, and end users.

Figure 3:
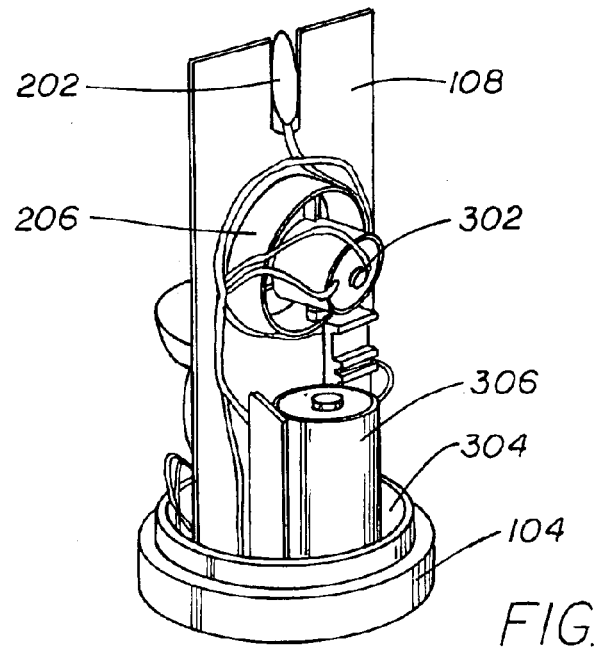
FIG. 3 is a rear perspective view of the flameless candle of FIG. 1 with the sidewall of the housing removed.

FIG. 3 shows a rear perspective view of flameless candle 100 with side wall 106 removed. Referring to FIGS. 1 and 3, motor 302 of fan 208 is positioned in air intake chamber 110. Base 104 and one end of wall 108 form compartment 304. Compartment 304, in one example, is utilized to house power source 306. Power source 306, in one example, drives fan 206 and/or light bulb 208. Power source 306 could be a C battery, D battery, AA battery, DC adaptor. In another example, compartment 304 could be used for storage of additional wicks, fragrance sources, etc.

Figure 4:
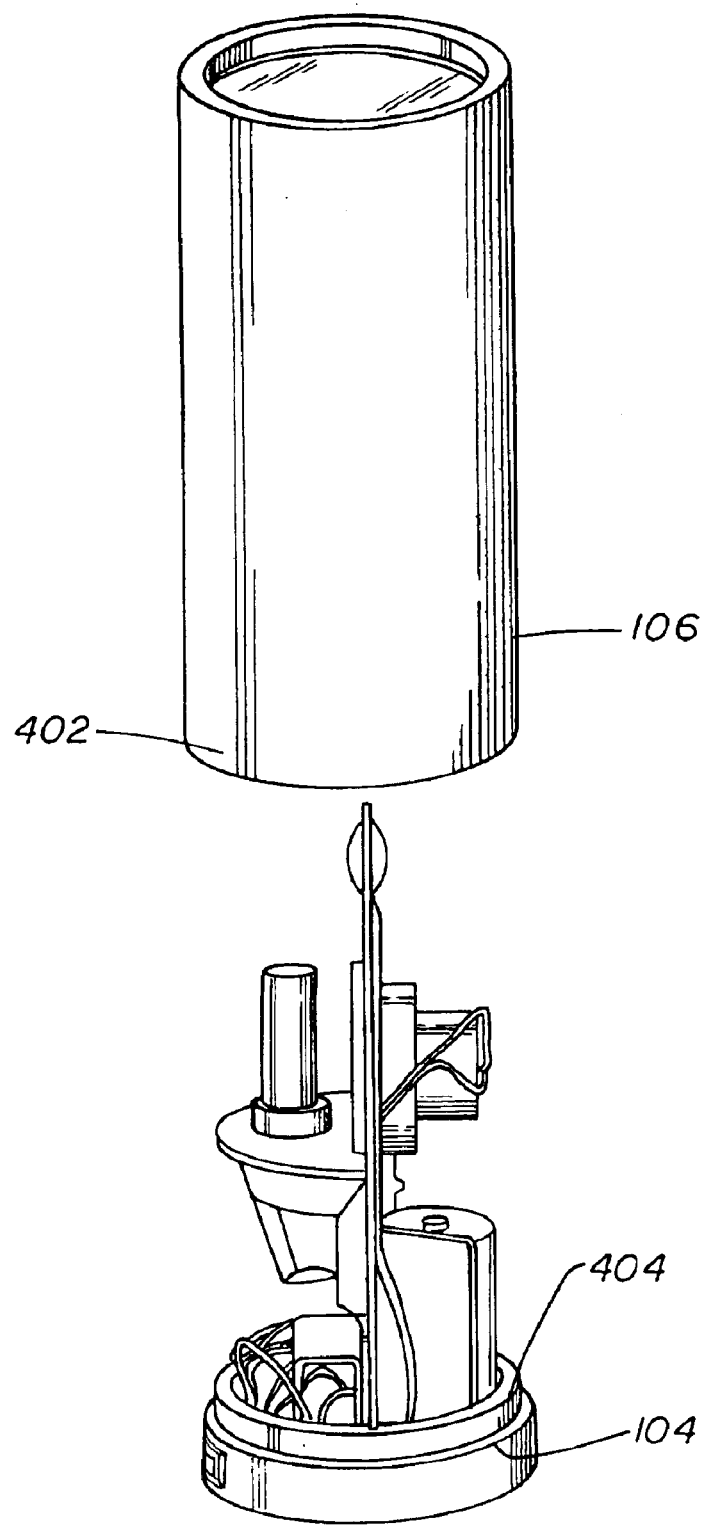
FIG. 4 is a partially exploded view of the flameless candle of FIG. 1.

Referring to FIG. 4, in one example, base 104 is circular and sidewall 106 is an open ended cylinder, although as it was previously noted flameless candle 100 could be any shape, in which case the shape of base 104 and sidewall 106 would be other than round. Base 104 and sidewall 106, in one example, are covered by wax. One end 402 of sidewall 106 is removeably connected to base 104. In one example, base 104 and sidewall 106 are frictionally engaged through utilization of ridge 404. Ridge 404 could have a slightly smaller diameter than sidewall 106. Accordingly, sidewall 106 would fit snuggly over ridge 404. Alternatively, ridge 404 could have a greater diameter than sidewall 106 and sidewall 106 would fit within ridge 404.

Figure 5:
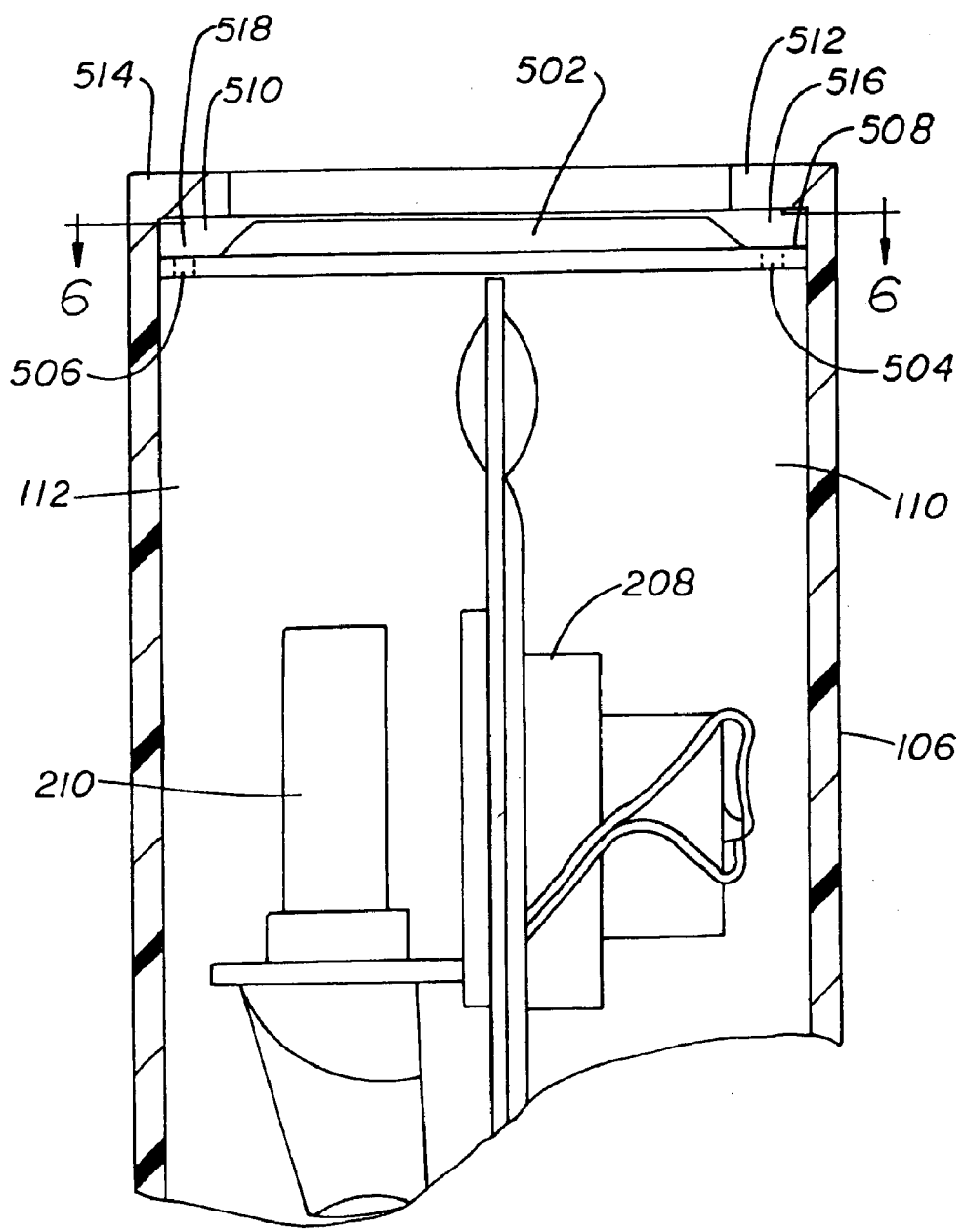
FIG. 5 is an enlarged partial side elevational view of a top portion of the flameless candle of FIG. 1 with the sidewall cut away.
Figure 6:
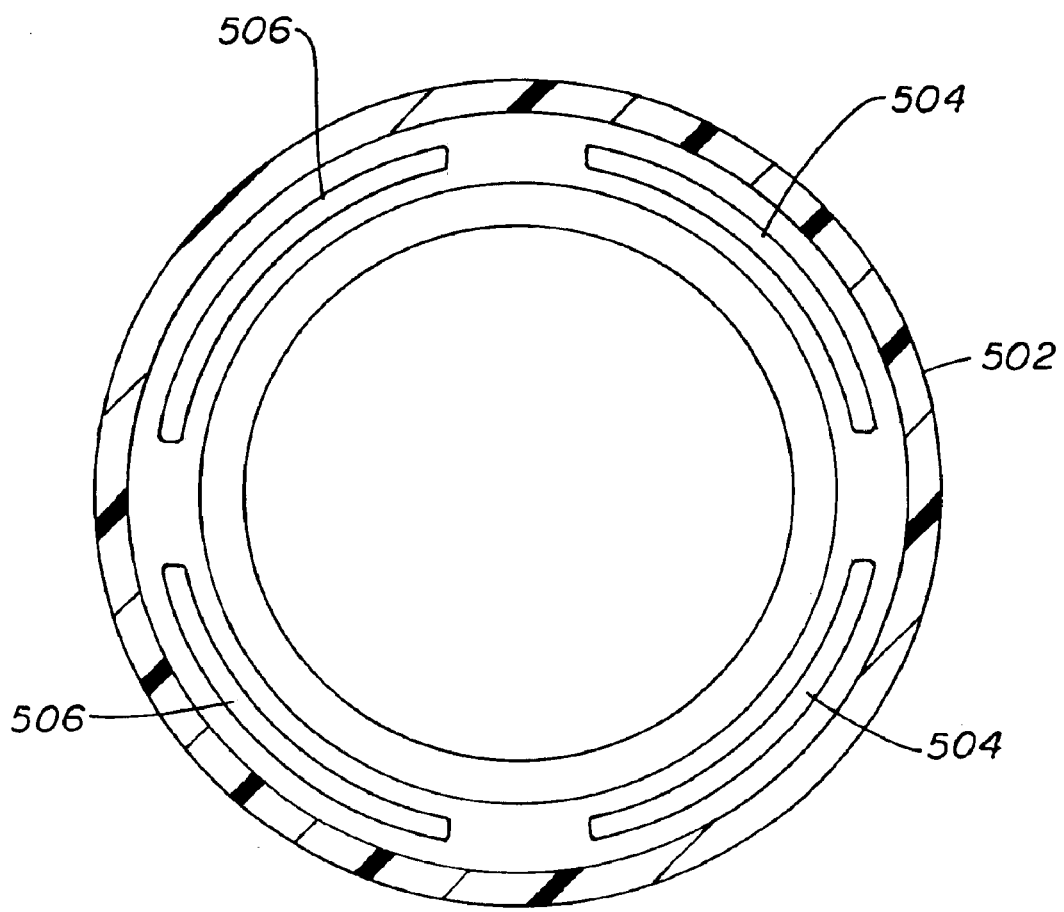
FIG. 6 is a top view of a lid that is shown attached to the housing of the flameless candle in FIG. 5.

Referring to FIGS. 5 and 6, lid 502, in one example, is positioned to at least partially cover air intake chamber 110 and air outflow chamber 112. Lid 502, in one example, is wax covered. Accordingly, an observer when looking down on flameless candle 101 would not observe the various components contained within flameless candle 100. Lid 502 includes openings 504, 506. Openings 504 register with air intake chamber 110 and openings 506 register with air outflow chamber 112.

Referring to FIG. 5, the portion of lid 502 containing slots 504, 506 is beveled to form beveled portions 508, 510. Beveled portions 508, 510 fit under top portions 512, 514 of sidewall 106, respectively. Beveled portions 508, 510 and top portions 512, 514 thereby form spaces 516, 518 which draw ambient air into air intake chamber 110 and expel fragrant air from air outflow chamber 112, respectively. Consequently, when fan 208 is on, ambient air is drawn into spaces 516 and through openings 504 into air intake chamber 110. Fan 208 creates an air stream over wick 210. Wick 210 deodorizes the air and fragrant air passes up air outflow chamber 112 through openings 506 and spaces 518 into the ambient air. Accordingly, the two chamber architecture described herein provides a concentrated directed air flow that efficiently draws air into and deposits fragrant air out of flameless candle 100.

Figure 7:
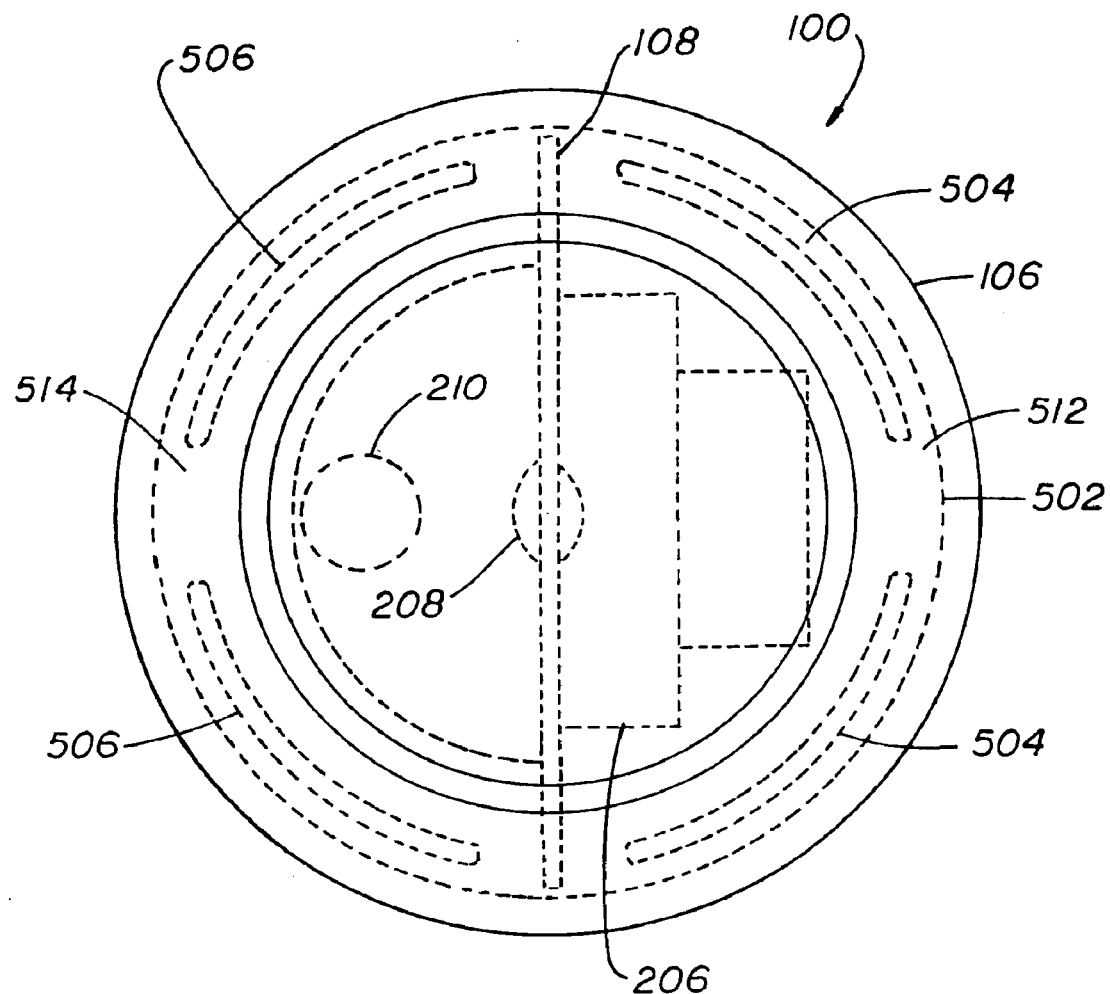
FIG. 7 is a top plan view of the flameless candle of FIG. 1 with internal components shown in phantom.

FIG. 7 shows a top plan view of flameless candle 100 with the interior components, such as fan 206, light bulb 208, and wick 210 shown in phantom. Because sidewall 106 and lid 502 are wax covered, and because top portions 512 and 514 of sidewall 106 cover openings 506, 508, an observer looking down on flameless candle 100 only will see what appears to be an ordinary candle.

Although exemplary embodiments of the invention have been depicted and described in detail herein, it will be apparent to those skilled in the relevant art that various modifications, additions, substitutions, and the like can be made without departing from the spirit of the invention and these are therefore considered to be within the scope of the invention as defined in the following claims.

What is claimed is:

1. A flameless candle, comprising:
   a housing defining an enclosure;
   a wall positioned in the enclosure forming an air intake chamber and an air outflow chamber;
   at least one opening proximate one end of the housing in communication with ambient air and the air intake chamber;
   at least one opening in communication with the air intake chamber and the air outflow chamber; and at least one opening proximate the one end of the housing in communication with the ambient air and the air outflow chamber.

2. The flameless candle of claim 1, wherein the housing, comprises:
a base; and
a sidewall.

3. The flameless candle of claim 2, wherein the sidewall is removably connected to the base.

4. The flameless candle of claim 2, wherein the base is circular and the sidewall is an open ended cylinder.

5. The flameless candle of claim 4, wherein the cylinder is wax covered.

6. The flameless candle of claim 2, wherein a plane of the base extends generally perpendicular to a plane of the sidewall.

7. The flameless candle of claim 2, wherein a plane of the base extends generally perpendicular to a plane of the wall.

8. The flameless candle of claim 2, wherein the wall includes one end connected to the base.

9. The flameless candle of claim 2, wherein the base is frictionally engaged with the sidewall.

10. A flameless candle, comprising:
a housing defining an enclosure and including a base and a sidewall;
a wall positioned in the enclosure forming an air intake-chamber and an air outflow chamber;
at least one opening in communication with ambient air and the air intake chamber;
at least one opening in communication with the air intake chamber and the air outflow chamber; and
at least one opening in communication with the ambient air and the air outflow chamber;
wherein the base comprises two opposing sides and the wall is positioned between the two opposing sides.

11. The flameless candle of claim 10, wherein the wall is positioned approximately equidistant from the two opposing sides.

12. A flameless candle, comprising:
a housing defining an enclosure;
a wall positioned in the enclosure forming an air intake chamber and an air outflow chamber;
at least one opening in communication with ambient air and the air intake chamber;
at least one opening in communication with the air intake chamber and the air outflow chamber;
at least one opening in communication with the ambient air and the air outflow chamber; and
a lid at least partially covering the air intake chamber and the air outflow chamber.

13. The flameless candle of claim 12, wherein the lid and the sidewall form the at least one opening in communication with ambient air and the air intake chamber and the at least one opening in communication with the ambient air and the air outflow chamber.

14. The flameless candle of claim 12, wherein the lid includes at least one opening in communication with the air intake chamber and at least one opening in communication with the air outflow chamber.

15. A flameless candle, comprising:
a housing defining an enclosure;
a wall positioned in the enclosure forming an air intake chamber and an air outflow chamber;
at least one opening in communication with ambient air and the air intake chamber;
at least one opening in the wall in communication with the air intake chamber and the air outflow chamber;
at least one opening in communication with the ambient air and the air outflow chamber;
a fan positioned in the at least one opening in the wall between the air intake chamber and the air outflow chamber to create an air stream wherein an intake of the fan draws air from the air intake chamber and deposits air in the air outflow chamber; and
a wick and fragrance source positioned in the air stream created by the fan.

16. The flameless candle of claim 15, wherein the wick and fragrance source are positioned in the air outflow chamber.

17. A flameless candle, comprising:
a housing defining an enclosure;
a wall positioned in the enclosure forming an air intake chamber and an air outflow chamber;
at least one opening in communication with ambient air and the air intake chamber;
at least one opening in communication with the air intake chamber and the air outflow chamber;
at least one opening in communication with the ambient air and the air outflow chamber;
a second opening in communication with the air intake chamber and the air outflow chamber; and
a light source positioned in the second opening.

18. A flameless candle comprising:
a fan that generates an air stream;
a wick positioned at least partially in the air stream; and
a wax covered sidewall defining an enclosure that contains the fan and the wick.

19. The flameless candle of claim 18, wherein the fan operates intermittently to create the air stream.

20. The flameless candle of claim 18, wherein the fan operates continuously to create the air stream.

21. The flameless candle of claim 18, further comprising:
a volatile fluid reservoir, wherein the wick is at least partially immersed in the volatile fluid reservoir.

22. The flameless candle of claim 18, further comprising:
a base that is engaged with the wax covered sidewall.

23. The flameless candle of claim 22, wherein the fan and the wick are mounted on the base.

24. The flameless candle of claim 22, further comprising:
a wall positioned in the enclosure.

25. The flameless candle of claim 24, wherein one end of the wall is connected to the base.

26. The flameless candle of claim 24, wherein the fan is mounted to the wall.

27. The flameless candle of claim 24, wherein the wick is mounted to the wall.

28. The flameless candle of claim 24, further comprising:
a light source mounted to the wall.

29. The flameless candle of claim 24, wherein the wax covered sidewall is an open ended cylinder.

30. A flameless candle comprising:
a wax covered housing defining an enclosure;
a wall positioned in the enclosure to form an air intake chamber and an air outflow chamber in the enclosure;
an opening in the wax covered housing that is in communication with the air intake chamber and the air outflow chamber; and
a lid positioned in the opening.

31. The flameless candle of claim 30, wherein the wax covered housing comprises a sidewall.

32. The flameless candle of claim 31, wherein the sidewall comprises two opposing sides.

33. The flameless candle of claim 32, further comprising:
a lid at least partially covering an opening on one end of the open ended cylinder.

34. The flameless candle of claim 33, wherein the lid and the sidewall form at least one opening that communicates with the enclosure.

35. The flameless candle of claim 33, wherein the lid includes at least one opening that communicates with the enclosure.

36. The flameless candle of claim 32, wherein the lid is spaced horizontally from the two opposing sides.

37. The flameless candle of claim 32, wherein the lid is spaced apart vertically from a top portion of the two opposing sides.

38. The flameless candle of claim 30, wherein the lid includes at least one opening in communication with the air intake chamber.

39. The flameless candle of claim 30, wherein the lid includes at least one opening in communication with the air outflow chamber.

40. A flameless candle comprising:
a housing including a sidewall defining an interior space;
a wax-like substance covering an exterior portion of the sidewall;
an opening in the housing;
a directional air moving device for creating an air stream through the opening; and
a fragrance source in the interior space for communication with the air stream.

41. The flameless candle of claim 40, wherein the air moving device includes a fan.

42. The flameless candle of claim 41, and further comprising a flameless light source at least partly within the interior space and visible from an exterior position.

43. A flameless candle comprising:
a housing defining an interior space;
an opening through the housing in air flow communication between the interior space and an exterior space;
a directional air moving device for creating an air stream from the interior space through the opening;
a fragrance source in the interior space for communication with the air stream; and
a flameless light source at least partly within the interior space and visible from the exterior space.

44. The flameless candle of claim 43, wherein the air moving device includes a fan.

45. The flameless candle of claim 44, and further comprising a wax-like substance covering an exterior portion of the housing.

46. A flameless candle comprising:
a directional air mover for generating an air stream;
a volatile dispersion member positioned to be at least partially in the air stream; and
a sidewall defining an enclosure that contains the directional air mover and the dispersion device, wherein the sidewall is at least partly covered with a wax-like substance.

47. The flameless candle of claim 46, wherein the directional air mover includes a fan.

48. The flameless candle of claim 46, wherein the volatile dispersion member includes a wick.

49. The flameless candle of claim 46, wherein the wax-like substance includes wax.

* * * * *

US006966665C1

(12) EX PARTE REEXAMINATION CERTIFICATE (7078th)
United States Patent
Limburg et al.

(10) Number: US 6,966,665 C1
(45) Certificate Issued: Sep. 22, 2009

(54) FLAMELESS CANDLE WITH AIR INTAKE CHAMBER AND AIR OUTFLOW CHAMBER

(75) Inventors: James A. Limburg, Racine, WI (US); Thomas J. Szymczak, Franksville, WI (US); Milan L. Zdrubecky, Milwaukee, WI (US)

(73) Assignee: S.C. Johnson & Son, Inc., Racine, WI (US)

Reexamination Request:
No. 90/008,694, Jun. 11, 2007

Reexamination Certificate for:
Patent No.: 6,966,665
Issued: Nov. 22, 2005
Appl. No.: 10/608,199
Filed: Jun. 27, 2003

(51) Int. Cl.
*F21V 33/00* (2006.01)

(52) U.S. Cl. ............... 362/96; 362/161; 362/392; 362/806

(58) Field of Classification Search .............. None
See application file for complete search history.

(56) References Cited

U.S. PATENT DOCUMENTS

| 4,301,783 | A |   | 11/1981 | Buckner et al. |
| 4,567,548 | A | * | 1/1986  | Schneeberger ............ 362/161 |
| 5,241,779 | A | * | 9/1993  | Lee ........................ 43/139 |
| 5,492,664 | A | * | 2/1996  | Cutts ....................... 264/156 |
| 6,413,476 | B1 |   | 7/2002  | Barnhart |
| 7,029,146 | B2 |   | 4/2006  | Kitchen |
| 7,132,084 | B1 |   | 11/2006 | Roumpos |
| 2003/0007887 | A1 |   | 1/2003 | Roumpos et al. |

OTHER PUBLICATIONS

Communication Pursuant to Article 96(2) EPC for Application No. 04 756 191.5–2423 dated Nov. 5, 2007.

* cited by examiner

*Primary Examiner*—Jeffrey L. Gellner

(57) ABSTRACT

A flameless candle includes a housing, which defines an enclosure. A wall is positioned in the enclosure to form an air intake chamber and an air outflow chamber. At least one opening is in communication with both the ambient air and the air intake chamber. At least one opening is in communication with the air intake chamber and the air outflow chamber. And at least one opening is in communication with the ambient air and the air outflow chamber.

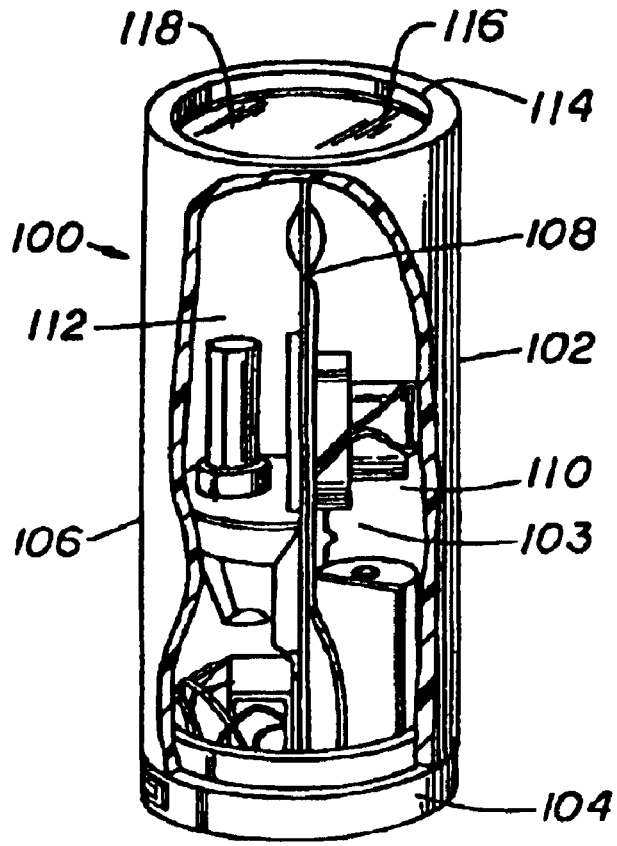

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 15–17 is confirmed.

Claims 2, 4, 5, 14, 22, 24, 26, 41 and 47 are cancelled.

Claims 1, 3, 6–10, 12, 18, 23, 25, 27–30, 40, 42, 43 and 46 are determined to be patentable as amended.

Claims 11, 13, 19–21, 31–39, 44, 45, 48, and 49, dependent on an amended claim, are determined to be patentable.

New claims 50–55 are added and determined to be patentable.

1. A flameless candle, comprising:
a housing defining an enclosure;
a wall positioned in the enclosure forming an air intake chamber and an air outflow chamber; at least one opening proximate one end of the housing in communication with ambient air and the air intake chamber;
at least one opening in communication with the air intake chamber and the air outflow chamber; and
at least one opening proximate the one end of the housing in communication with the ambient air and the air outflow chamber,
*wherein the housing comprises a base and a sidewall, the base is circular and the sidewall is an open ended cylinder, and wherein the cylinder is wax covered.*

3. The flameless candle of claim [2] *1*, wherein the sidewall is removably connected to the base.

6. The flameless candle of claim [2] *1*, wherein a plane of the base extends generally perpendicular to a plane of the sidewall.

7. The flameless candle of claim [2] *1*, wherein a plane of the base extends generally perpendicular to a plane of the wall.

8. The flameless candle of claim [2] *1*, wherein the wall includes one end connected to the base.

9. The flameless candle of claim [2] *1*, wherein the base is frictionally engaged with the sidewall.

10. A flameless candle, comprising:
a housing defining an enclosure and including a base and a sidewall;
a wall positioned in the enclosure forming an air intake-chamber and an air outflow chamber;
at least one opening in communication with ambient air and the air intake chamber;
at least one opening in communication with the air intake chamber and the air outflow chamber; [and]
at least one opening in communication with the ambient air and the air outflow chamber; *and*
*a light source disposed inside the housing;*
wherein the base comprises two opposing sides and the wall is positioned between the two opposing sides, *and wherein the at least one opening in communication with the air intake chamber and the air outflow chamber allows light from the light source to be evenly distributed throughout the enclosure.*

12. A flameless candle, comprising:
a housing defining an enclosure;
a wall positioned in the enclosure forming an air intake chamber and an air outflow chamber;
at least one opening in communication with ambient air and the air intake chamber;
at least one opening in communication with the air intake chamber and the air outflow chamber;
at least one opening in communication with the ambient air and the air outflow chamber; and
a lid at least partially covering the air intake chamber and the air outflow chamber;
*wherein the lid includes at least one opening in communication with the air intake chamber and at least one opening in communication with the air outflow chamber.*

18. A flameless candle comprising:
a fan that generates an air stream;
a wick positioned at least partially in the air stream; [and]
a wax covered sidewall defining an enclosure that contains the fan and the wick;
*a base that is engaged with the wax covered sidewall; and*
*a wall positioned in the enclosure, wherein the fan is mounted to the wall.*

23. The flameless candle of claim [22] *18*, wherein the fan and the wick are mounted on the base.

25. The flameless candle of claim [24] *18*, wherein one end of the wall is connected to the base.

27. The flameless candle of claim [24] *18*, wherein the wick is mounted to the wall.

28. The flameless candle of claim [24] *18*, further comprising a light source mounted to the wall.

29. The flameless candle of claim [24] *18*, wherein the wax covered sidewall is an open ended cylinder.

30. A flameless candle comprising:
a wax covered housing defining an enclosure;
a wall positioned in the enclosure to form an air intake chamber and an air outflow chamber in the enclosure;
an opening in the wax covered housing that is in communication with the air intake chamber and the air outflow chamber *and a second opening defined in the wall between the air intake chamber and the air outflow chamber*; and a lid positioned in the opening.

40. A flameless candle comprising:
a housing including a sidewall defining an interior space;
a wax-like substance covering an exterior portion of the sidewall;
*a wall positioned in the interior space forming an air intake chamber and an air outflow chamber, wherein the wall defines an aperture extending between the air inflow chamber and the air outflow chamber;*
an opening in the housing;
a [directional air moving device for creating] *fan that creates* an air stream through the opening *and the aperture*; and
a fragrance source in the interior space [for] *in* communication with the air stream;

wherein the air stream moves a fragrance compound from the fragrance source through the opening into the ambient air at room temperature.

42. The flameless candle of claim [41] *40*, and further comprising a flameless light source at least partly within the interior space and visible from an exterior position.

43. A flameless candle comprising:

a housing defining an interior space;

an opening through the housing in air flow communication between the interior space and an exterior space;

a directional air moving device for creating an air stream from the interior space through the opening;

a fragrance source in the interior space for communication with the air stream; [and]

a flameless light source at least partly within the interior space and visible from the exterior space*; and*

*a lid covering the opening, wherein the lid includes a first opening in communication with an air intake chamber and a second opening in communication with an air outflow chamber*.

46. A flameless candle comprising:

a [directional air mover for generating] *fan that creates* an air stream;

a volatile dispersion member positioned to be at least partially in the air stream; [and]

a sidewall *and a lid* defining an enclosure that contains the [directional air mover] *fan* and the dispersion device, wherein the sidewall is at least partly covered with a wax-like substance *and wherein the air stream moves a volatile active from the volatile dispersion member into the ambient air at room temperature; and*

*at least two openings through the enclosure defined by the lid.*

*50. The flameless candle of claim 15, wherein the fragrance source comprises a volatile liquid.*

*51. The flameless candle of claim 15, wherein the wick comprises an ultrahigh molecular weight high density polyethylene.*

*52. The flameless candle of claim 15 further comprising a light source disposed inside the housing.*

*53. The flameless candle of claim 10, wherein the base is circular and the sidewall is cylindrical.*

*54. The flameless candle of claim 17, wherein the air intake chamber and the air outflow chamber are shaped differently from one another.*

*55. The flameless candle of claim 17, wherein one of the air intake chamber and the air outflow chamber is an upper chamber and the other of the air intake chamber and the air outflow chamber is a lower chamber.*

* * * * *